United States Patent [19]

Kachel et al.

[11] 4,198,160
[45] Apr. 15, 1980

[54] APPARATUS FOR PERFORMING AT LEAST TWO MEASUREMENTS OF CHARACTERISTICS IN A PARTICLE SUSPENSION

[75] Inventors: Volker Kachel, Puchheim; Ewald Glossner, München, both of Fed. Rep. of Germany

[73] Assignee: Max-Planck-Gesellschaft zur Förderung der Wissenschaften e.V., Göttingen, Fed. Rep. of Germany

[21] Appl. No.: 858,310

[22] Filed: Dec. 7, 1977

[30] Foreign Application Priority Data

Dec. 14, 1976 [DE] Fed. Rep. of Germany ....... 2656654

[51] Int. Cl.² ...................... G01N 21/52; G01N 27/08
[52] U.S. Cl. .................................. 356/72; 324/71 CP; 356/317
[58] Field of Search ............... 356/72, 73, 317, 318, 356/342; 324/71 CP

[56] References Cited

U.S. PATENT DOCUMENTS

| | | | |
|---|---|---|---|
| 3,361,965 | 1/1968 | Coulter et al. | 324/71 CP |
| 3,738,759 | 6/1973 | Dittrich et al. | 356/342 |
| 3,761,187 | 9/1973 | Dittrich et al. | 356/246 |
| 3,770,349 | 11/1973 | Legorreta-Sanchez | 356/73 |
| 3,910,702 | 10/1975 | Corll | 356/72 |
| 4,014,611 | 3/1977 | Simpson et al. | 356/72 |
| 4,070,617 | 1/1978 | Kachel et al. | 324/71 CP |

Primary Examiner—Vincent P. McGraw
Attorney, Agent, or Firm—Edwin E. Greigg

[57] ABSTRACT

An apparatus for performing at least two measurements of characteristics in a suspension of particles, including two chambers separated by a measuring orifice through which the suspension of particles flows in response to a pressure difference between the two chambers. A glass plate is disposed a short distance beyond the measuring orifice in the direction of flow and at right angles to the direction of flow, and diverts the flow at substantially right angles to its flow direction through the measuring orifice. An optical measuring device is provided and situated coaxially with the flow through the measuring orifice and downstream of the glass plate. The optical measuring device produces an irradiation of the particles in suspension and the fluorescence thereby induced is measured. Another measurement is achieved by measuring a voltage pulse utilizing a pair of electrodes, one in each of the two chambers. The voltage pulse is varied as a function of the particle size passing the measuring orifice. The amplitude of the voltage pulse is therefore a measure of the volume of the particle. The measurements are made simultaneously.

4 Claims, 6 Drawing Figures

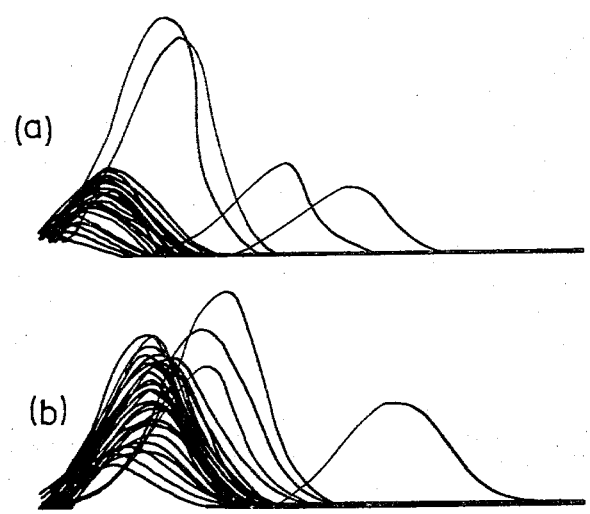
Fig. 4  (1 cm ≙ 20µs)
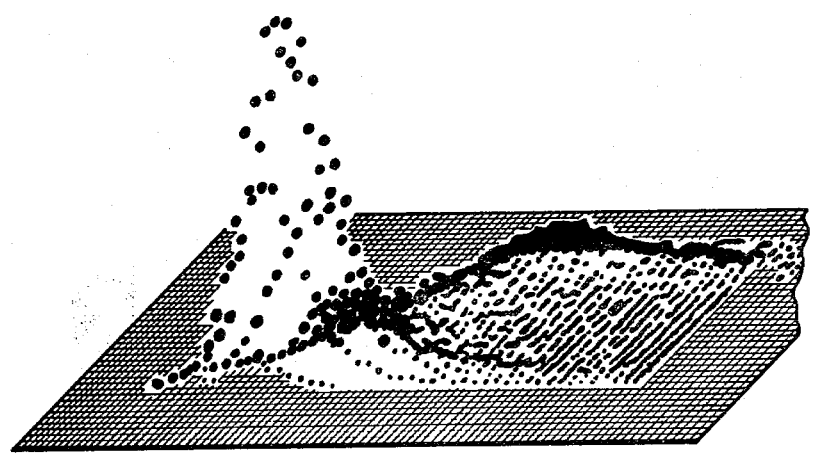
Fig. 5

APPARATUS FOR PERFORMING AT LEAST TWO MEASUREMENTS OF CHARACTERISTICS IN A PARTICLE SUSPENSION

BACKGROUND OF THE INVENTION

The invention relates to an apparatus for performing at least two measurements of characteristics in a particle suspension.

Such apparatuses are known, for example, from U.S. Pat. No. 3,710,933; and the article by Steinkamp et al., in Rev. Sci. Instrum., Volume 44, No. 9, September 1973, pages 1301–1310, cf. particularly FIG. 2 on page 1302.

What is involved is a combination of a measurement in accordance with the Coulter principle involving a fluorescence measurement with the aid of an optical device, the filamentary particle stream being upstream of a measuring aperture in which the volume is measured, and conducted past observation windows, through an exciting radiation, e.g., a laser radiation is radiated onto the particles, with the fluorescence induced in the course thereof being measured; at the same place the measurement of the light scattering may also be made. Thus, two parameters, viz. the volume and the fluorescence, are measured at two measuring locations arranged one behind the other. For the purpose of the evaluation, it is important to coordinate the results of the measurement of one parameter with the results of the measurement of the other parameter. In the evaluation of the measuring results measured at the two measuring locations, account must be taken of the time of the passage of the particles between the two measuring locations (cf. in this connection U.S. Pat. No. 3,710,933, column 10, lines 31-34). This involves a grave disadvantage; the time of passage, which has to be accurately adjusted, depends particularly on a variety of influencing parameters, e.g., velocity of flow of the medium, temperature, pressure differentials, etc., all of which are sources of possible measuring errors.

OBJECTS AND SUMMARY OF THE INVENTION

The object of the invention is to create an apparatus of the kind hereinbefore mentioned, in which falsifications of the evaluation of the measuring results of two measurements in consequence of times of passage, which vary or are not accurately determinable, of the particles between the two measuring locations at which the various measurements are taken, are practically eliminated.

In the known apparatuses hereinbefore mentioned, the improvements which can be made by arranging the two measuring locations as closely together as possible, are not adequate.

According to the present invention, the noted object is achieved by an arrangement having two chambers separated by a measuring orifice through which a suspension of particles flows due to a pressure difference existing between the chambers. Two electrodes are provided, one for each of the two chambers, a glass plate to divert flow of the suspension of particles after it leaves the measuring orifice and an optical measuring device. With this arrangement, at least two measurements of characteristics in the suspension of particles are taken.

By means of such an arrangement, it is possible to perform the measurements in accordance with the Coulter principle and the optical measurement at practically one location, viz. in the plane of the lower end (in the direction of flow) of the measuring orifice. The pulse for the optical measurement practically coincides with the trailing edge of the pulse of the volume measurement in the measuring aperture, so that an unambiguous and errorless assignment of the measuring results corresponding to the two parameters to a particular particle becomes possible. The unambiguous coordination of two measurement values of a particle also permits the establishment of an unambiguous relationship therebetween. If, for example, the fluorescence of a particle is proportional to its content of a particular active ingredient (e.g., RNS), it is possible to determine the concentration of the active ingredients in the particles from the measured quantity and the volume. This can be done by means of a simple arithmetic unit.

Although it is known per se to divert the stream which transports the particles through substantially a right angle after its discharge from a nozzle or bore and, in this manner, to form a measuring location for the optical system (see in this regard German Offenlegungsshrifts or laid-open applications Nos. 1,815,352 and 1,919,628), these apparatuses do not involve two measurements, one of which is performed in accordance with the Coulter principle; neither do they suggest this, since they explicitly regard the measurement of the volume in accordance with the Coulter principle as being too inaccurate and substitutes therefor a photometric measurement (cf. German Offenlegungsshrift No. 1,815,352, Page 3, lines et seq.) No solutions to the aforesaid problem of taking account of the time of passage of a particle between the two different measuring locations in apparatuses of the kind hereinbefore stated can be gleaned therefrom.

BRIEF DESCRIPTION OF THE DRAWINGS

An exemplary embodiment of the invention and of its advantageous development are hereinafter described with reference to the accompanying drawings, in which:

FIG. 4 illustrates the photographic results of the image of a plurality of pulses according to FIG. 3 taken on an oscillograph;

FIG. 5 illustrates the photographic results of the image of a 2-parameter-multi-channel analyzer, which shows the measuring results for the volume and the fluorescence of a specimen of cultivated nerve cells of rats;

DESCRIPTION OF THE PREFERRED EMBODIMENT

Figure 1:
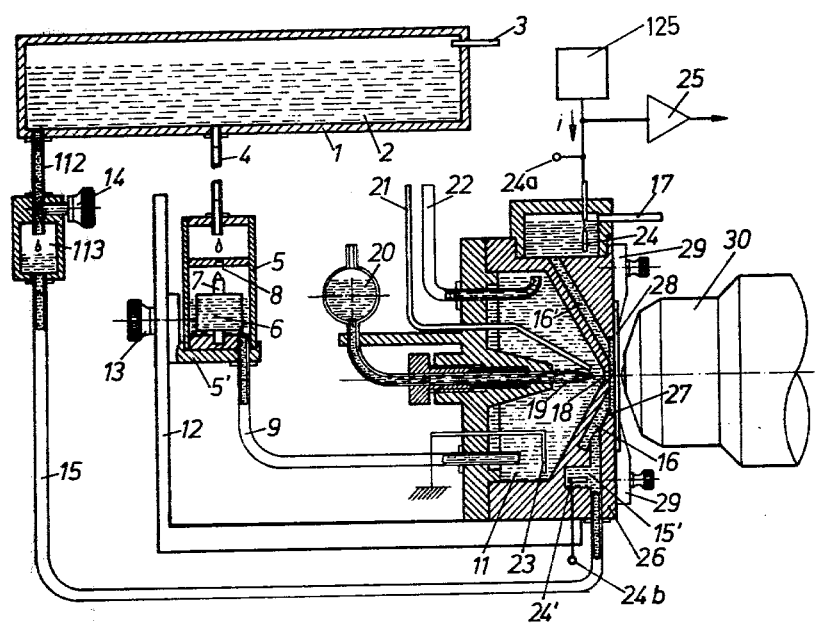
FIG. 1 shows an exemplary embodiment.

The apparatus according to FIG. 1 consists of a tank 1 for a particle-free electrolyte 2 with a vent 3, which is, via a conduit 4, in communication with a first dropping or drip chamber 5. In the latter, a float 6 having a needle 7 is provided, so that as the liquid level rises, the needle 7 closes the aperture 8. As a result, a galvanic separation is produced between the electrolyte in the drip chamber 5 and in the tank 1, and at the same time the maintenance of a predetermined value for the liquid level in the drip chamber—with respect to the support plate 5', is achieved. The drip chamber 5 is, via the conduit 9, in communication with a chamber 11 and continuously supplies electrolyte to the latter. Moreover the height of the drip chamber 5 is adjustable and settable on a rail 12 by means of a screw 13. Since the level of the electrolyte in the drip chamber 5 is always constant, the pressure in the chamber 11 can be adjusted by means of this height adjustment of the drip chamber 5. The tank 1 is moreover in communication with a chamber 16 via a second conduit 112, a second dropping or drip chamber 113 and a further conduit 15. The conduit 112 may be interrupted by means of a screw clamp 14. The connection opens initially into a somewhat enlarged antechamber 15'. Via this connection the chamber 16 is continuously supplied with electrolyte. The chamber 16 moreover has a discharge pipe 17 to which a source of subatmospheric pressure (not shown) is applied, which produces a predetermined degree of suction. The first chamber 11 and the second chamber 16 moreover communicate via a measuring orifice 18. Close upstream of the measuring orifice 18 is disposed the discharge opening of a capillary tube 19 which serves the purpose of supplying a particle suspension. The particle suspension is contained in a container 20 which communicates with the capillary tube 19. In the chamber 11 there if further provided a rinsing capillary 21 and a vent pipe 22.

Figure 2:
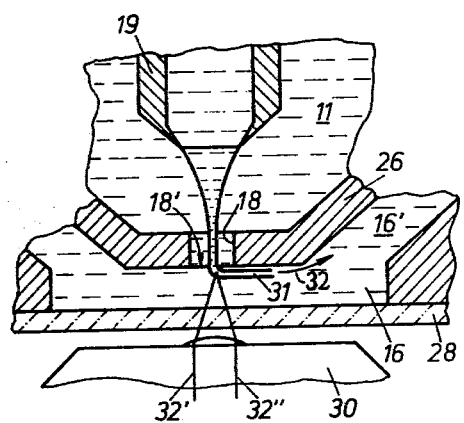
FIG. 2 shows a part of the exemplary embodiment according to FIG. 1.

If now provision is made, by means of suitable adjustment of the sub-atmospheric pressure at the discharge pipe 17, for the pressure in the first chamber 11 to be higher than that in the second chamber 16, then electrolyte flows from the chamber 11 through the measuring orifice 18 into the chamber 16. This flow becomes narrower upstream of the measuring orifice 18. If moreover the pressure of the particle suspension in the capillary tube 19 is somewhat greater than in the chamber 11, then the particle suspension is discharged from the capillary tube 19 into the stream which tapers towards the measuring orifice 18 and is made narrower thereby (hydrodynamic focussing) and transported through the measuring orifice 18 (FIG. 2). In the chamber 11 a first electrode 23 and in the chamber 16 a second electrode 24 are provided. The electrode 24' in the antechamber 15' is connected in parallel with the electrode 24 by reason of the associated terminals 24a and 24b being interconnected. Between the two a current i which is imposed by a current source 125 flows. When a particle passes through the measuring orifice 18, a displacement of the electric field and thus a variation in resistance takes place in the measuring orifice 18, which, when the current i is imposed, results in a voltage pulse between the electrodes 23, 24. The amplitude of the voltage pulse $u_v$ (FIG. 3) is a measure of the volume of the particle. This voltage pulse is amplified in an amplifier 25 and conducted to an evaluation unit (not shown) which classifies and evaluates the pulses according to their amplitude.

The chamber 16 is arranged in a block 26. The chamber 16 has an aperture 27, which is covered by a glass plate 28. Beyond the glass plate 28 an optical system 30 is provided. The provision and disposition of this optical system 30 is such that the particles emanating from the measuring orifice 18 are disposed in the range of satisfactory definition of the optical system. On the properties of the optical system also depends the distance between the rear end (in the direction of flow) 18' from the glass plate 28; it is, for example, 100µ-30 mm. By means of this optical system 30 the particles are irradiated by an exciting radiation, e.g., a laser radiation. By means of the same optical system the fluorescence thereby induced is measured. Such optical systems are known, so that a more detailed description thereof may, in the present case, be dispensed with. Thereby, as already mentioned the fluorescence is for example measured; moreover the light scattering may also be measured therewith. The pulses $u_f$ (see FIG. 3) measured by this optical system 30 are also classified and evaluated in the evaluation device (not shown).

As shown in FIG. 2, the filamentary particle stream 31 is diverted through substantially a right angle at its discharge from the rear end 18' (in the direction of flow) of the measuring orifice 18. After the diversion the filamentary particle stream 31 finally follows the direction of the arrow 32; thereafter its precise course is no longer of interest. The particle suspension reaches the region 16' of the chamber 16 at the upper portion of the chamber, in which the discharge pipe 17 is provided. The optical system 30 is focussed onto the rear end 18' of the measuring orifice, as indicated by the rays 32', 32".

Firstly, the measurement of the volume upon the passage through the measuring orifice 18 takes place practically simultaneously with the measurement of the fluorescence by the optical system 30. It should be added that a plurality of measurements (fluorescence, light scattering) may of course also be made simultaneously by means of the optical system.

Figure 3:
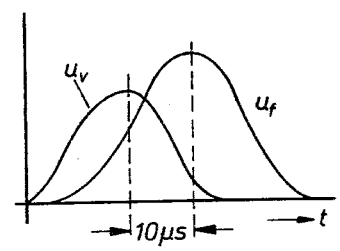
FIG. 3 shows, as a function of time, the two pulses, which result from the measurement of the volume and of the fluorescence of a particle.

As can be seen from FIG. 3, the pulse $u_f$ which is a measure of the fluorescence of a particle, coincides practically with the rear flank of the somewhat longer pulse $u_v$ which is produced at the electrodes 23, 24 and which is a measure of the volume of the particle. Thereby an unambiguous coordination between the pulses from the point of view of time is made possible. FIG. 4 shows a photograph of the representation of such pulses on an oscillograph, which confirms this.

Provision is made for the particle stream itself not to come into contact with the glass plate 28 so as to soil it, despite the diversion of the stream. This is achieved by means of the stream of the electrolyte supplied via the conduit 15, which performs the function of a rinsing stream to the extent that it carries along with it the filamentary particle flow emanating from the measuring orifice 18 into the region 16' of the chamber 16. The electrode 24' in the antechamber 15' serves the purpose of avoiding, at the end of the measuring aperture 18, any excessive and one-sided concentration of lines of force in the very confined region between the end 18' of the measuring orifice and the glass plate 28.

FIG. 5 is a photographic reproduction of an image of a 2-parameter-multi-channel analyser. It shows the profile of the volume and fluorescence measurement of a particular particle quantity, displayed on the screen of such an instrument. What was measured is the parameter-fluorescence and volume in the case of cultivated nerve cells of rats, which in part are in the state of cell division, Mithramycin, which fluoresces, being deposited on the DNS which is synthesised in the course of the division. A very large number of cells has a low volume and a low degree of fluorescence. This is the first high crest of the mountain range-like representation in the left hand front portion of the image. These cells are in their so-called G1-phase, in which the DNS-content of the cells remains constant. In the region of increasing fluorescence the number of the cells decreases. The plateau which follows characterizes the so-called synthesis phases S, in which DNS is synthesised in preparation for the subsequent cell division, the volume also decreasing slightly. Shortly ahead of and during the division phase (G2-phase) the cells then coincide with the second small peak obliquely to the rear in the representation 4, i.e., the number of these cells is again somewhat larger. This example shows, that satisfactory 2-parameter-measurements can be performed by means of the apparatus embodying the invention.

Figure 6:
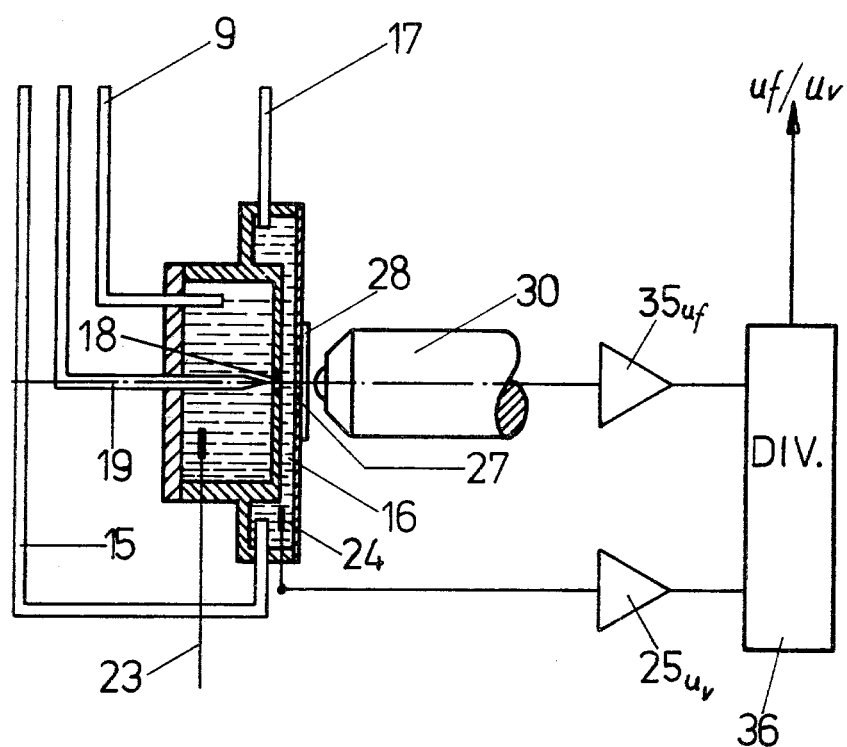
FIG. 6 is a block diagram of a particular application of the invention.

FIG. 6 shows a representation of the principles of an apparatus according to FIGS. 1 to 3. A measuring pulse derived from the optical measuring device 30 is amplified in the amplifier 35. The amplified measuring pulse $u_f$ is supplied to a divider 36. The measuring pulse $u_v$ which has been amplified in the amplifier 25 is also supplied to the divider 36. In the divider 36 the quotient $u_f/u_v$ is formed. This is the volume concentration of a particular active ingredient of a particle on the assumption that $u_f$ i.e., the fluorescence, is proportional to the quantity of the active ingredient of the particle. This is, for example, the case where RNS is concerned.

What is claimed is:

1. An apparatus for performing a measurement of the volume and the fluorescence of particles suspended in a suspension of particles, comprising:
   means defining a first and second chamber and a measuring orifice interconnecting said chambers;
   a first electrode disposed in said first chamber;
   a second electrode disposed in said second chamber;
   a capillary tube disposed in said first chamber and defining a discharge orifice at one end thereof which is located upstream of the measuring orifice, said capillary tube being coaxially, with respect to said orifice, arranged to introduce a suspension of particles into the flow of an electrolyte and through the measuring orifice, the arrangement being such that the flow of particles included in the electrolyte takes place through the measuring orifice as a result of the pressure difference between the first and second chambers;
   an fluorescence measuring device situated downstream of and coaxially with the measuring orifice along the path of flow of the particles;
   a glass plate situated between the measuring orifice and the fluorescence measuring device, and at right angles to the axis of the measuring orifice, said glass plate being adapted to divert the flow of the particles through substantially a right-angle.

2. The apparatus as defined in claim 1, further comprising:
   means for supplying a cleaning stream to the second chamber downstream of the measuring orifice and substantially at right-angles to the axis of the measuring orifice, to thereby conduct the flow of the particles in the direction of the diversion produced by the glass plate.

3. The apparatus as defined in claim 1, further comprising:
   a third electrode, said second and third electrodes being disposed in the second chamber downstream of the measuring orifice and on opposite sides of the axis of the measuring orifice, said third electrode being connected in parallel with said second electrode.

4. The apparatus as defined in claim 1, further comprising:
   an arithmetic unit electrically connected to the optical measuring device and to the electrodes, said arithmetic unit being adapted to divide a signal supplied by the optical measuring device by a signal supplied by the electrodes and supply a signal representing the result of the division.

* * * * *